US006191174B1

(12) United States Patent
Early et al.

(10) Patent No.: US 6,191,174 B1
(45) Date of Patent: Feb. 20, 2001

(54) PROCESS AND PLANT FOR THE PRODUCTION OF METHANOL

(75) Inventors: Simon Robert Early, London; Timothy Douglas Gamlin, Woking; Mark Andrew Linthwaite, Twickenham, all of (GB)

(73) Assignee: Kvaerner Process Technology Limited, London (GB)

( * ) Notice: Under 35 U.S.C. 154(b), the term of this patent shall be extended for 0 days.

(21) Appl. No.: 09/117,861

(22) PCT Filed: Dec. 11, 1997

(86) PCT No.: PCT/GB97/03413

§ 371 Date: Aug. 7, 1998

§ 102(e) Date: Aug. 7, 1998

(87) PCT Pub. No.: WO98/28248

PCT Pub. Date: Jul. 2, 1998

(30) Foreign Application Priority Data

Dec. 20, 1996 (EP) .................................................. 96309421

(51) Int. Cl.$^7$ ............................. C07C 27/00; B01J 10/00
(52) U.S. Cl. ......................... 518/705; 518/700; 518/702; 518/704; 422/188; 422/189; 422/236; 422/239
(58) Field of Search .................................... 518/705, 704, 518/702, 700; 422/188, 189, 236, 239

(56) References Cited

U.S. PATENT DOCUMENTS

| 3,186,145 | 6/1965 | Pelton et al. ............................. 55/43 |
| 3,215,502 | 11/1965 | Korwin .................................... 23/277 |
| 3,442,002 | 5/1969 | Geary, Jr. et al. ...................... 29/450 |
| 3,531,263 | 9/1970 | Sederquist ................................ 48/61 |
| 3,598,527 | 8/1971 | Quarrulli et al. ....................... 23/199 |
| 3,909,299 | 9/1975 | Corrigan ................................. 136/86 |
| 3,940,428 | 2/1976 | Connell et al. ...................... 260/449.5 |
| 3,950,369 | 4/1976 | Gent ................................... 260/449.5 |
| 4,051,300 | 9/1977 | Klein et al. ............................ 428/398 |
| 4,098,588 | 7/1978 | Buswell et al. ........................... 48/94 |
| 4,181,675 | 1/1980 | Makin et al. ....................... 260/449.5 |
| 4,423,022 | 12/1983 | Albano et al. ........................ 423/360 |
| 4,529,738 | 7/1985 | Sugier et al. .......................... 518/700 |
| 4,595,701 | 6/1986 | Nakamura et al. .................... 518/701 |
| 4,692,306 | 9/1987 | Minet et al. ............................ 422/49 |
| 4,782,096 | * 11/1988 | Banquy ................................. 518/704 |
| 4,849,187 | 7/1989 | Uozu et al. ........................... 422/197 |
| 4,861,348 | 8/1989 | Koyama et al. .......................... 48/94 |
| 4,909,808 | 3/1990 | Voecks ..................................... 48/94 |
| 4,968,722 | 11/1990 | Westerterp ............................ 518/706 |
| 5,063,250 | 11/1991 | Murayama et al. .................... 518/704 |
| 5,106,590 | 4/1992 | Hopper et al. ........................ 422/198 |
| 5,264,008 | 11/1993 | Corrigan ................................. 48/94 |
| 5,472,986 | * 12/1995 | Van Dijk ................................ 518/705 |
| 5,523,326 | 6/1996 | Dandekar et al. .................... 548/706 |

FOREIGN PATENT DOCUMENTS

| 0 033 128 | 8/1981 | (EP) ................................. C01B/3/38 |
| WO 94/29013 | 12/1994 | (WO) ............................... B01J/8/06 |
| WO 96/21634 | 7/1996 | (WO) ........................... C07C/29/151 |

OTHER PUBLICATIONS

International Search Report, PCT/GB97/03413, Jun. 4, 1998 (4 pages).

Holm–Larsen et al. "Autothermal Reforming Turns Methanol Plant Off–Gas into a Low Cost Feedstock" Ammonia/Methanol Synthesis, *Nitrogen*, No. 222, pp. 37–40, (Jul.–Aug. 1996).

Translation of German Patent No. P 32 44 302.1 dated May 30, 1984, 15 pages.

* cited by examiner

Primary Examiner—Paul J. Killos
Assistant Examiner—J. Parsa
(74) *Attorney, Agent, or Firm*—Senniger, Powers, Leavitt & Roedel

(57) ABSTRACT

The present invention relates to a process for the production of methanol from a hydrocarbon feedstock comprising: contacting a vaporous mixture comprising the feedstock and steam in a steam reforming zone with a catalyst effective for catalysis of at least one reforming reaction; recovering from the reforming zone a synthesis gas mixture comprising carbon oxides, hydrogen and methane; supplying material of the synthesis gas mixture to a methanol synthesis zone charged with a methanol synthesis catalyst and maintained under methanol synthesis conditions; recovering from the methanol synthesis zone a product gas mixture comprising methanol and unreacted material of the synthesis gas mixture; supplying material of the product gas mixture to a methanol recovery zone maintained under methanol recovery conditions; recovering from the methanol recovery zone a crude methanol product stream and a vaporous steam comprising unreacted material of the synthesis gas mixture; separating material of the synthesis gas mixture into a first hydrogen-rich stream and a second hydrogen-depleted stream comprising carbon oxides and methane; supplying at least part of the first hydrogen-rich stream to the steam reforming zone as fuel; and recycling at least part of the second hydrogen-depleted stream to the steam reforming zone to form part of the mixture of the vaporous mixture comprising the feedstock and steam and to a plant constructed and arranged so as to be operable in accordance with the process.

19 Claims, 4 Drawing Sheets

PROCESS AND PLANT FOR THE PRODUCTION OF METHANOL

This application is a 371 of PCT/GB97/03413 filed on Dec. 11, 1997.

FIELD OF THE INVENTION

This invention relates to a process and plant for the production of methanol.

BACKGROUND OF THE INVENTION

Methanol is synthesised in large volumes annually by conversion of a carbonaceous feedstock, usually a hydrocarbonaceous feedstock such as natural gas, into a mixture of carbon oxides and hydrogen. Such a mixture of gases is often referred to as synthesis gas.

The conversion of a hydrocarbon-containing feedstock, such as natural gas, into synthesis gas can be effected by steam reforming.

In steam reforming a mixture of desulphurised hydrocarbon feedstock, such as natural gas, and steam is passed at high temperature, typically at a temperature of from about 600° C. to about 1000° C., and elevated pressure, typically from about 10 bar up to about 50 bar, over a suitable reforming catalyst, such as a supported nickel catalyst. One commercially recommended catalyst which can be used for this purpose uses a mixture of calcium and aluminium oxides as support for the nickel. When natural gas is the feedstock, the principal reaction is:

$$CH_4 + H_2O \rightleftharpoons CO + 3H_2$$

The reaction products themselves are further subject to the reversible "water gas shift" reaction in which carbon dioxide and hydrogen are produced from carbon monoxide and steam:

$$CO + H_2O \rightleftharpoons CO_2 H_2$$

Conversion of the carbon oxides and hydrogen to methanol occurs according to the following reactions:

$$CO + 2H_2 \rightleftharpoons CH_3OH$$

$$CO_2 + 3H_2 \rightleftharpoons CH_3OH + H_2O$$

These reactions are conventionally carried out by contacting the synthesis gas with a suitable methanol synthesis catalyst under an elevated synthesis gas pressure, typically in the range of from about 50 bar up to about 100 bar, usually about 80 bar, and at an elevated methanol synthesis temperature, typically from about 210° C. to about 270° C. or higher, e.g. up to about 300° C.

A conventional methanol synthesis plant can be considered to comprise four distinct parts, namely:

1. a reforming plant, which produces a mixture of carbon oxides and hydrogen from a hydrocarbon feedstock;
2. a compression stage lifting the carbon oxides and hydrogen mixture to a higher pressure suitable for downstream methanol synthesis;
3. a methanol synthesis section, in which crude methanol is produced from the carbon oxides and hydrogen; and
4. a distillation section, in which the final refined methanol product is produced from the crude methanol.

Such a plant is described, for example, in WO-A-96/21634.

In order to achieve high yields of methanol, prior art processes have commonly included a recycle loop around the methanol synthesis zone so that unreacted materials leaving the methanol synthesis zone are recycled to the methanol synthesis zone. Thus, U.S. Pat. No. 4,968,722 relates to a process for the production of methanol by reacting carbon monoxide and hydrogen in which the reactants are introduced into a methanol synthesis zone comprising one or more fixed catalyst beds. The effluent from the methanol synthesis zone is fed to an absorption zone where methanol is absorbed. Unreacted reactants are fed to a further methanol synthesis and recovery zone.

U.S. Pat. No. 5,472,986 discloses a methanol production process in which hydrogen is recovered by use of a membrane from a purge gas taken from the methanol synthesis zone. The purged and separated hydrogen is recycled to the methanol synthesis zone as a reactant for methanol synthesis.

U.S. Pat. No. 4,181,675 relates to a methanol synthesis process in which synthesis gas is passed over a methanol synthesis catalyst in a methanol synthesis zone and is then cooled to condense methanol. The remaining gas is recycled to the methanol synthesis zone. A purge stream from this recycle stream may be passed through a membrane to control any build up of inert gases in the recycle stream. Inert materials are separated from carbon oxide and hydrogen, the latter being supplied to the methanol synthesis zone as reactants for methanol synthesis.

DE-A-3244302 discloses a process for the production of methanol in which unreacted methanol synthesis gas is supplied to a three-way separation stage. In the separation stage, CO is separated and recycled to the methanol synthesis zone; $CO_2$ is separated and supplied to the reforming zone in order to replace part of the water vapour required for reforming; and a residual gas comprising hydrogen, nitogen and methane is supplied to the reforming zone as fuel to heat the reformer tubes.

Various other methanol Production processes are known in the art, and reference may be made, for example, to U.S. Pat. No. 5,063,250, U.S. Pat. No. 4,529,738, U.S. Pat. No. 4,595,701, U.S. Pat. No. 5,063,250, U.S. Pat. No. 5,523,326, U.S. Pat. No. 3,186,145, U.S. Pat. No. 344,002, U.S. Pat. No. 3,598,527, U.S. Pat. No. 3,940,428, U.S. Pat. No. 3,950,369 and U.S. Pat. No. 4,051,300.

A number of different types of reformer are known in the art. One such type is known as a "compact reformer" and is described in WO-A-94/29013, which discloses a compact endothermic reaction apparatus in which a plurality of metallic reaction tubes are close-packed inside a reformer vessel. Fuel is burned inside the vessel, which comprises air and fuel distribution means to avoid excessive localised heating of the reaction tubes. In a compact reformer of this type heat is transferred from the flue gas vent and from the reformed gas vent of the reformer to incoming feedstock, fuel and combustion air. Other types of reformer are not as efficient as the compact reformer in transferring heat internally in this way. However, many other reformer designs are known and some are described in EP-A-0033128, U.S. Pat. No. 3,531,263, U.S. Pat. No. 3,215,502, U.S. Pat. No. 3,909,299, U.S. Pat. No. 4,098,588, U.S. Pat. No. 4,692,306, U.S. Pat. No. 4,861,348, U.S. Pat. No. 4,849,187, U.S. Pat. No. 4,909,808, U.S. Pat. No. 4,423,022, U.S. Pat. No. 5,106,590 and U.S. Pat. No. 5,264,008.

In a conventional plant, synthesis gas is compressed in passage from the reforming plant to the methanol synthesis zone. The synthesis gas compression stage is essentially present in order to provide the required pressure of from 50 bar to 100 bar in the methanol synthesis zone. The synthesis gas compressor is an expensive item which has a significant impact on the overall cost of the plant. Furthermore, the presence in the plant of synthesis gas at such high pressures necessitates the use in the plant of thick walled stainless steel or alloyed steel high pressure pipework. This pipework is expensive to buy, to weld and to use as a construction material. It therefore represents a substantial financial cost in the building of the plant.

BRIEF SUMMARY OF THE INVENTION

It is an object of the invention to provide a plant for methanol production which is cost-efficient to build and which avoids the use of at least some of the expensive components hitherto favoured in conventional methanol plants. A further object of the invention is to provide a process for the production of methanol which is carbon-efficient, providing good yields of methanol and which does not rely essentially on the use of very high pressure in the methanol synthesis zone. It is yet another object of the invention to provide a methanol production plant which is suitable for construction and operation in remote or offshore locations.

According to the present invention, there is provided a plant for the production of methanol from a hydrocarbon feedstock material comprising:

a) a steam reforming zone, adapted to be maintained under steam reforming conditions and charged with a catalyst effective for catalysis of at least one steam reforming reaction, for steam reforming of a vaporous mixture of the hydrocarbon feedstock and steam to form a synthesis gas mixture comprising carbon oxides, hydrogen and methane;

b) a methanol synthesis zone, adapted to be maintained under methanol synthesis conditions and charged with a methanol synthesis catalyst, for conversion of material of the synthesis gas mixture to a product gas mixture comprising product methanol and unreacted material of the synthesis gas mixture;

c) a methanol recovery zone, adapted to be maintained under methanol recovery conditions, for recovery of a crude methanol product stream from the product gas mixture, and for recovery of a vaporous stream comprising unreacted material of the synthesis gas mixture;

d) a separation zone for separation of material of the synthesis gas mixture into a first hydrogen-rich stream and a second hydrogen-depleted stream comprising carbon oxides and methane;

e) means for supplying at least part of the first hydrogen-rich stream to the steam reforming zone as fuel; and f) means for recycling at least part of the second hydrogen-depleted stream to the reforming zone for admixture with the vaporous mixture of hydrocarbon feedstock and steam.

The separation of the first hydrogen-rich stream from the second hydrogen-depleted stream may occur upstream or downstream of the methanol synthesis zone. Thus, in one preferred embodiment of the invention the separation zone is located downstream of the methanol synthesis zone, means being provided for supplying the at least part of the second hydrogen-depleted stream from the separation zone to the reforming zone without passing through the methanol synthesis zone. In an alternative embodiment of the invention, the separation zone is located upstream of the methanol synthesis zone, means being provided for supplying the at least part of the second hydrogen-depleted stream to the methanol synthesis zone and thereafter recovering an unreacted part of the second hydrogen-depleted stream and supplying the unreacted part to the reforming zone.

Usually, the carbon oxides referred to will comprise a mixture of CO and $CO_2$.

The invention further provides a process for the production of methanol from a hydrocarbon feedstock comprising:

a) contacting a vaporous mixture comprising the feedstock and steam in a steam reforming zone with a catalyst effective for catalysis of at least one reforming reaction;

b) recovering from the reforming zone a synthesis gas mixture comprising carbon oxides, hydrogen and methane;

c) supplying material of the synthesis gas mixture to a methanol synthesis zone charged with a methanol synthesis catalyst and maintained under methanol synthesis conditions;

d) recovering from the methanol synthesis zone a product gas mixture comprising methanol and unreacted material of the synthesis gas mixture;

e) supplying material of the product gas mixture to a methanol recovery zone maintained under methanol recovery conditions;

f) recovering from the methanol recovery zone a crude methanol product stream and a vaporous stream comprising unreacted material of the synthesis gas mixture;

g) separating material of the synthesis gas mixture into a first hydrogen-rich stream and a second hydrogen-depleted stream comprising carbon oxides and methane;

h) supplying at least part of the first hydrogen-rich stream to the steam reforming zone as fuel; and i) recycling at least part of the second hydrogen-depleted stream to the steam reforming zone to form part of the mixture of step a)

The separation step may take place upstream or downstream of the methanol synthesis zone. Thus, it may be preferred that the separation step g) takes place downstream of the methanol synthesis zone, the at least part of the second hydrogen-depleted stream being supplied from the separation step g) to the reforming zone without passing through the methanol synthesis zone. Alternatively, it may be preferred that the separation step g) takes place upstream of the methanol synthesis zone, the at least part of the second hydrogen-depleted stream being supplied to the methanol synthesis zone, an unreacted part of the second hydrogen-depleted stream being recovered thereafter and supplied to the reforming zone.

The process and plant of the invention have significant advantages over conventional plants and processes for the production of methanol, as will now be described.

The process and plant of the invention operate such that unreacted carbon oxides and methane recovered from the methanol synthesis zone are, after separation from hydrogen, recycled as feedstock to the reforming zone. Hydrogen recovered from the separation zone is supplied to the reforming zone as fuel. This arrangement differs from prior art arrangements in which unconverted synthesis gas, usually after enrichment in either hydrogen or carbon oxides, is recycled to the methanol synthesis zone and has a number of significant advantages over such prior art processes. In the process and plant of the invention, there is provided a recycle circuit for unconverted carbon-containing compounds, the reforming zone and the methanol synthesis zone being inside the same recycle circuit. By "carbon-containing compounds" is meant principally carbon oxides, methane, or mixtures thereof. By "carbon oxides" is meant principally carbon monoxide and carbon dioxide.

The recycle of unconverted carbon oxides and methane to the reforming zone means that, overall, the process of the invention is highly carbon efficient, with little or no carbon being lost from the process, regardless of the conversion yields obtained in either or both of the reforming zone and the methanol synthesis zone. Thus, the operator of a plant designed in accordance with the invention has the option to operate the process of the invention at relatively low conversion yields per pass in one or both of the reforming zone and the methanol synthesis zone. This has potential cost-saving advantages. For example, the methanol synthesis zone may be operated at lower pressure and/or with a smaller catalyst volume than in conventional processes.

In the steam reforming zone of a plant according to the invention and operated in accordance with the process of the invention, the degree of conversion of the feedstock to synthesis gas may be maintained at a low level, relative to conventional plants, because the hydrogen-depleted stream comprising unreacted carbon oxides and methane is recycled as feedstock to the reforming zone in any event. The synthesis gas mixture recovered from the steam reforming zone in the plant and process of the invention comprises hydrogen, carbon oxides and methane. If the steam reforming zone is maintained under conditions such that the overall conversion of hydrocarbon feedstock to carbon oxides and hydrogen is relatively low, methane will be present in the synthesis gas mixture in larger quantities than if the conversion is high, in which case methane will be present in relatively smaller quantities in the synthesis gas mixture. This is the case regardless of whether the hydrocarbon feedstock is predominantly methane (as in natural gas) or whether the hydrocarbon feedstock is predominantly composed of some higher hydrocarbon. Higher hydrocarbons which are not steam reformed to carbon oxides and hydrogen are hydrocracked under the steam reforming conditions to methane. Thus, an ethane feedstock, a propane feedstock or a mixed butane/methane feedstock, for example, will reform to give a mixture of carbon oxides, hydrogen and methane.

In conventional plants, it is desirable to ensure that reforming of hydrocarbon to carbon oxides and hydrogen is as complete as possible. Thus, because low pressure favours the steam reforming reactions, it is desirable in conventional plants to maintain the reforming zone under a relatively low pressure, for example about 20 bar. Whilst it is certainly possible to operate the process and plant of the invention such that a pressure of about 20 bar is used in the reforming zone, in practice it is a desirable feature of the invention that higher reforming pressures, for example from about 25 bar to about 50 bar, for example about 30 bar can be used. This has important advantages downstream of the reforming zone. In conventional processes, a make up gas compressor is used to compress the synthesis gas mixture entering the methanol synthesis loop. In addition, a recycle compressor is provided within the loop to circulate unreacted synthesis gas therein. In the process of the invention, because the reforming zone is included within a recycle circuit it is possible to provide a single compressor to drive the supply of the make-up gas to the methanol synthesis zone and the recirculation of unreacted synthesis gas around the circuit. Moreover, the provision of a single circuit including the reformer means that the position of the compressor may be selected by the designer of the plant as desired. When only one compressor is used in this way, the plant of the invention may be significantly more compact than prior art plants. Thus, driving equipment and pipework associated with multiple compression in the prior art is much reduced. This is significant because the plant of the invention may be built conveniently in remote, even offshore, locations. It has not hitherto been possible economically to construct a commercial methanol plant in an offshore location.

It is therefore an important feature of the present invention that the unreacted material of the synthesis gas mixture recovered from the methanol recovery zone, or the material of the synthesis gas mixture recovered from the reforming zone as the case may be, comprises hydrogen, carbon oxides and methane and is separated into a hydrogen-rich stream, which is supplied as fuel to the steam reforming zone, and a hydrogen-depleted stream, comprising carbon oxides and methane, which is recycled to the steam reforming zone for admixture with the feedstock. The plant and process of the invention therefore includes the reforming zone, the methanol synthesis zone, the methanol recovery zone and the separation zone inside one carbon oxide and methane recycle circuit. This arrangement enables the plant and process of the invention to be operated with a single compression stage driving the flow of materials around the recycle circuit. The compression stage may be provided at any convenient location inside the recycle circuit, the position of the compressor depending upon the balance between capital and operating costs of the plant. This contrasts with conventional processes, in which unconverted carbon oxides are recycled to the front end of the methanol synthesis zone and a recycle compressor must be provided to maintain the pressure or the recycle stream at the high pressures used in conventional methanol synthesis plants. In conventional processes, it is not desirable to have a large quantity of methane present in this recycle stream and so a purge stream may be taken to control any build up of methane present in the synthesis gas mixture as a result of incomplete reaction in a reforming zone.

When the degree of conversion in the reforming zone is maintained at a relatively low level, this has little or no impact on the overall methanol yield of a process in accordance with the invention because unconverted methane is recycled to the reforming zone in any event. This enables the use, in the process and plant of the invention, of a relatively low steam to carbon ratio and/or a relatively low outlet temperature in the reforming zone. Thus, in the process of the invention the steam to carbon ratio in the steam reforming zone is preferably less than about 3:1, even more preferably less than about 2.8:1, for example about 2.5:1 or less. The outlet temperature of the reforming zone, by which is meant the temperature at the exit end of the reforming catalyst inside the zone, may range from about 700° C. to about 1000° C., for example about 850° C. The use of a lower reforming temperature, compared to conventional plants, allows the operator of a plant and process according to the invention to use a relatively high reforming pressure, for example a reforming pressure of more than about: 20 bar, for example about 30 bar or about 40 bar or more. In particular, the use of a "compact reformer", as described in WO-A-94/29013, operated at relatively low temperatures and relatively high pressures allows a plant according to the invention to be significantly more compact than conventional plants. This is significant because a plant according to the invention may conveniently be built in remote, even offshore, locations. It has not hitherto been possible economically to construct a commercial methanol plant in an offshore location.

The process and plant of the invention have great flexibility and may be designed such that in the methanol synthesis zone the conversion yield per pass of carbon oxides to methanol is from about 40% to about 95% or higher, preferably from 70% to 90% for example about 80%.

The process and plant of the present invention preferably utilise pressures of from about 20 bar to about 50 bar, e.g. from about 35 bar to about 45 bar, e.g. about 40 bar in the methanol synthesis zone.

The use of relatively low pressures in the methanol synthesis zone has the further advantage that the cost of building a plant in accordance with the invention is significantly reduced, relative to conventional plants, by avoiding the need to use thick-walled, high pressure pipework.

In conventional plants, a synthesis gas compressor is required to drive the synthesis gas into the methanol synthesis zone at a pressure of about 80 bar. Typically, the motive force for gas compression is provided by high pressure steam generated within the plant by a steam turbine. The plant and process of the invention may be operated at much lower pressures, as has been explained above. The process of the invention can use a smaller compressor than has been used in prior art processes. The pressure in the methanol synthesis zone of the plant of the invention may be provided by a single compression stage which may be located at any suitable position inside the recycle circuit.

The possibility to operate the plant of the invention with only one relatively small compressor has ramifications beyond cost. The absence of any associated steam turbine, steam generation and transfer system, significantly reduces the size of a plant according to the invention, in relation to conventional plants. This reduction in size allows the plant of the invention to be constructed economically in remote or offshore locations.

In conventional plants, the fuel used in the steam reforming zone is generally a hydrocarbon feedstock material which may contain sulphurous impurities such as hydrogen sulphide. In the plant and process of the present invention, the separated hydrogen-rich stream is supplied as fuel to the reforming zone. The flue gas from the reforming zone of a plant according to the invention is therefore substantially sulphur free and can, if desired, be cooled below its dew point for immediate disposal, without the need for further treatment to remove sulphurous acids, as may be required in conventional plants.

If desired, a purge stream may be taken from the carbon oxide and methane containing recycle stream. The purge stream may be supplied as fuel to the reforming zone. Usually, a purge stream will be taken, the rate of purge being selected to control any accumulation in the recycle circuit of chemically inert materials, such as nitrogen, argon and helium, that may be present in the feedstock material.

In a preferred plant and process of the invention, the separation zone comprises a membrane separator which may be of any suitable design. A number of membrane separators suitable for use in the process and plant of the present invention are described in U.S. Pat. No. 4,181,675, referred to hereinabove.

It is further preferred that the methanol synthesis zone comprise a number of methanol synthesis reactors connected in series. A methanol recovery zone may be provided between each successive methanol synthesis reactor and after the last methanol synthesis reactor in the series. A vaporous carbon oxide and hydrogen-containing stream from each methanol recovery zone, other than the last in the series, is supplied to a next successive methanol synthesis reactor in the series. The methanol synthesis reactions are equilibrium limited and this arrangement has the advantage that methanol is removed from the reaction mixture between each methanol synthesis reactor, thereby favouring the methanol forming reactions in the next successive methanol synthesis reactor.

Methanol recovery may be achieved by any suitable method, such as chilling or solvent washing. If solvent washing is chosen, suitable solvents include ethylene glycol, tetraethyleneglycol dimethyl ether, water and the like.

Conveniently, the or each crude methanol product stream is supplied to a refining zone for recovery of a refined methanol product stream. The refining zone may be remotely located from the plant. Thus, if the plant is constructed in an offshore location, a crude methanol product containing about 6% water may be recovered from the methanol recovery zone and shipped ashore for subsequent refining.

Desirably, a single gas compressor is provided to drive the feedstock, synthesis gas and vaporous carbon oxide and hydrogen-containing streams. The plant and process of the invention may be operated using a single stage compressor when the methanol synthesis pressure is maintained at or beneath about 50 bar. If methanol synthesis pressures of over about 50 bar are required, it may become desirable to employ a second compressor. The use of a single compressor has beneficial effects on the cost of building a plant in accordance with the invention and also on the space occupied by such a plant. The use of a single compressor in combination with a compact reformer, of the type mentioned above, enables a plant according to the invention to be economically constructed and operated at an offshore location. The provision of offshore methanol synthesis facilities is an important aspect of the invention and represents a significant improvement on conventional reformer based methanol synthesis technology, which cannot currently be provided offshore on a cost-effective basis.

The methanol synthesis zone is preferably maintained at a temperature of from about 210° C. to about 300° C., e.g. about 230° C. to about 270° C., e.g. about 240° C.

In a preferred process according to the invention, in which the reforming zone is a compact reforming zone of the type hereinbefore described, combustion air supplied to the reforming zone is saturated or partially saturated with water vapour before being supplied to the reforming zone. This has the advantage of modifying the combustion characteristics within the reforming zone, giving a more even heating of reforming elements within the zone and a reduction in emissions of nitrogen oxides, and carbon dioxide in the flue gas, relative to conventional plants.

In a preferred plant according to the invention the reforming zone is a compact reforming zone of the type hereinbefore described. However, the steam reforming zone used in the process and plant of the invention may be of any suitable design.

A preferred feedstock for use in the process of the invention is natural gas.

An advantageous feature of the plant and process of the invention is that the flue gas from the steam-reforming zone contains significantly lower quantities of carbon oxides and sulphur-containing compounds than a conventional plant of equivalent methanol production capacity.

In order that the invention may be clearly understood and readily carried into effect, a number of methanol synthesis plants constructed and arranged in accordance with the invention and designed to operate a preferred process in accordance with the invention will now be described, by way of example only, with reference to the accompanying diagrammatic drawings, in which:

DETAILED DESCRIPTION OF THE INVENTION

It will be understood by those skilled in the art that the drawings are diagrammatic and that further items of equipment such as reflux drums, pumps, vacuum pumps, temperature sensors, pressure sensors, pressure relief valves, control valves, Flow controllers, level controllers, holding tanks, storage tanks, and the like may be required in a commercial plant. The provision of such ancillary items of equipment forms no part of the present invention and is in accordance with conventional chemical engineering practice.

Figure 1:
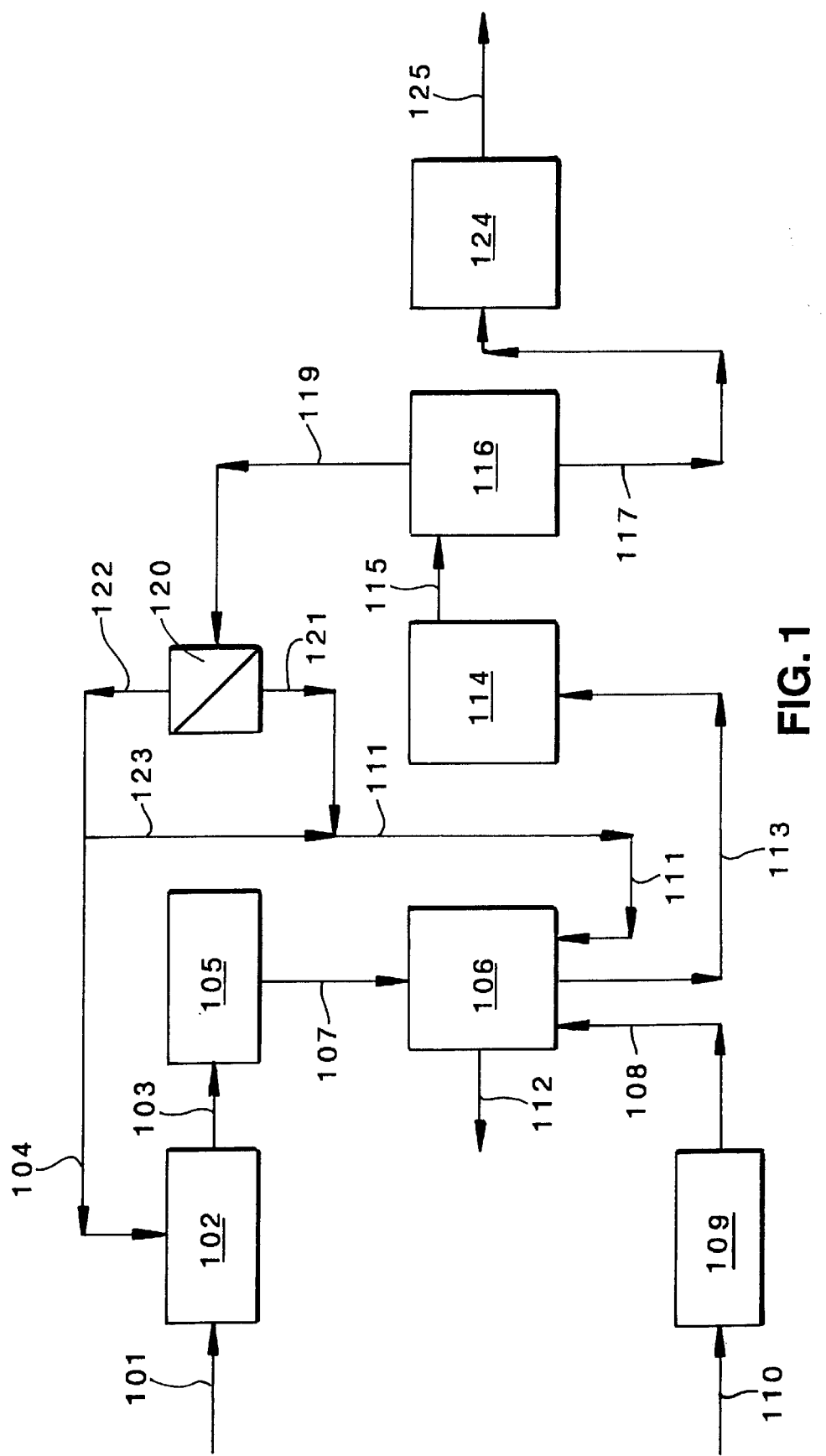
FIG. 1 is a simplified flow diagram of diagram of a first methanol synthesis plant according to the invention.

Referring to FIG. 1, a stream of natural gas is supplied in line 101 and, after passing through natural gas compressor 102, passes on in line 103 at a pressure of around 40 bar. Feedstock compressor 102 is further supplied with a recycle stream of carbon oxides and methane from line 104, as will be explained later.

The compressed feedstock and recycle stream in line 103 is supplied to a feed pretreatment zone 105. In feed pretreatment zone 105, the details of which are not shown in FIG. 1, the compressed stream is heated to around 380° C. before passing on to a desulphurisation reactor. The natural gas feedstock contains a minor amount or sulphur as hydrogen sulphide which is a poison to downstream catalysts. Sulphur is removed in passage through the desulphurisation reactor which contains a charge of desulphurisation materials, such as nickel molybdate and zinc oxide.

The desulphurised gas is cooled by passage through an interchanger and flows into the bottom of a saturator column in which the gas flows countercurrent to hot water supplied to the top of the saturator column.

In passage through the saturator column the gas mixture is saturated with water vapour. The water vapour-saturated gas mixture exits the saturator at about 200° C. and contains approximately 90% of the steam required for subsequent reforming. The gas/steam mixture is mixed with further steam supplied from a gas turbine and passes on through a mixed feed heater which is mounted in the flue gas duct of reformer 106. In passage through the mixed feed heater the temperature of the gas/steam mixture is raised to about 400° C. The resulting hot gas is fed in line 107 to reformer 106.

The detail of reformer 106 is not shown in FIG. 1. The reformer is preferably of the compact type hereinbefore described. Hot gas from line 107 is fed into the reaction tubes of compact reformer 106 which are packed with a suitable steam reforming catalyst, for example a supported nickel catalyst. The heat required to drive the endothermic reforming reactions is supplied by burning a hydrogen-rich fuel inside compact reformer 106, thus transferring heat to the reaction tubes by radiation and convection.

Reformer 106 is fed with hot combustion air from line 108, which is pre-heated in a combustion air pre-heater (not shown) heated by reformed gas inside compact reformer 106 and pre-compressed in combustion air compressor 109 after being supplied to the plant in line 110. Hydrogen to fuel reformer 106 is supplied in line 111 from a downstream separation step, as will be explained later. Hydrogen is combusted inside reformer 106, thus supplying radiant and convective heat to the reformer reaction tubes. Flue gas is vented from reformer 106 in line 112.

In compact reformer 106 the feed mixture of natural gas, steam and recycled carbon oxides is reformed to a mixture of carbon monoxide, carbon dioxide, hydrogen and methane, a mixture commonly known as synthesis gas.

In the presence of the nickel catalyst at elevated temperatures, steam reacts with vaporous hydrocarbons at elevated temperatures and pressures to give a synthesis gas consisting of carbon dioxide, carbon monoxide, and hydrogen, together with methane. The concentration of each constituent in the synthesis gas depends on the ratio of steam to hydrocarbon passing over the catalyst, and on the temperature and pressure at which the gases leave the catalyst. The reactions taking place are complex but the end product is determined by two reactions, i.e.

(i) the water gas shift equilibrium reaction:

$$CO + H_2O \leftrightarrows CO_2 + H_2 + Heat$$

(ii) the steam-methane equilibrium reaction $$Heat + CH_4 + H_2O \leftrightarrows CO + H_2$$

Overall the reactions are endothermic. A large excess of steam and a high temperature are required to move the equilibrium to the right and to reduce the residual methane content of the synthesis gas.

The synthesis gas leaves compact reformer 106 in line 113 at about 450° C. and about 30 bar. In operation sufficient carbon oxides and/or methane are preferably introduced through line 104 to provide a stoichiometric synthesis gas in line 113; hence the rate of carbon oxide and/or methane recycle may be controlled so that, on a molar basis, the hydrogen content is equal to twice the carbon monoxide content plus three times the carbon dioxide content.

The hot synthesis gas is cooled and passes by way of line 113 to methanol converter 114.

Typical methanol synthesis conditions in accordance with the invention include use of a pressure in the region of 30 bar and an outlet temperature of from about 210° C. to about 240° C. using a copper/zinc catalyst, for example the catalysts sold as ICI 51-7, Haldor Topsoe MK-101 or Sud-Chemie C79-5GL.

The methanol synthesis equilibria are as follows:

$$CO + 2H_2 \leftrightarrows CH_3OH$$

$$CO_2 + 3H_2 \leftrightarrows CH_3OH + H_2O$$

Typically, the gas in line 113 contains about 10 to about 20 vol % carbon oxides, the balance being hydrogen, methane and nitrogen. Nitrogen can be present as an impurity in the natural gas feedstock.

A product mixture is recovered in line 115 and passed to a methanol wash column 116, from which a crude methanol product is recovered in line 117. Unreacted synthesis gas from wash column 116 is supplied in line 119 to a separation zone 120.

Separation zone 120 can operate using any convenient known technique, for example pressure swing absorption, membrane technology, liquefaction, or a combination of two or more thereof. The use of membrane technology is preferred, often being the most economical.

A hydrogen-rich recycle stream is recovered in line 121 and supplied in line 111 as fuel to compact reformer 106. A carbon oxide and/or methane-rich stream is recovered in line 122 and supplied to line 104 as a recycle stream for admixture with the feedstock. A purge may be taken in line 123 to control any build up of inert materials.

Crude methanol product in line 117 is supplied to a refining zone 124, from which is recovered a refined methanol product in line 125.

Figure 2A:
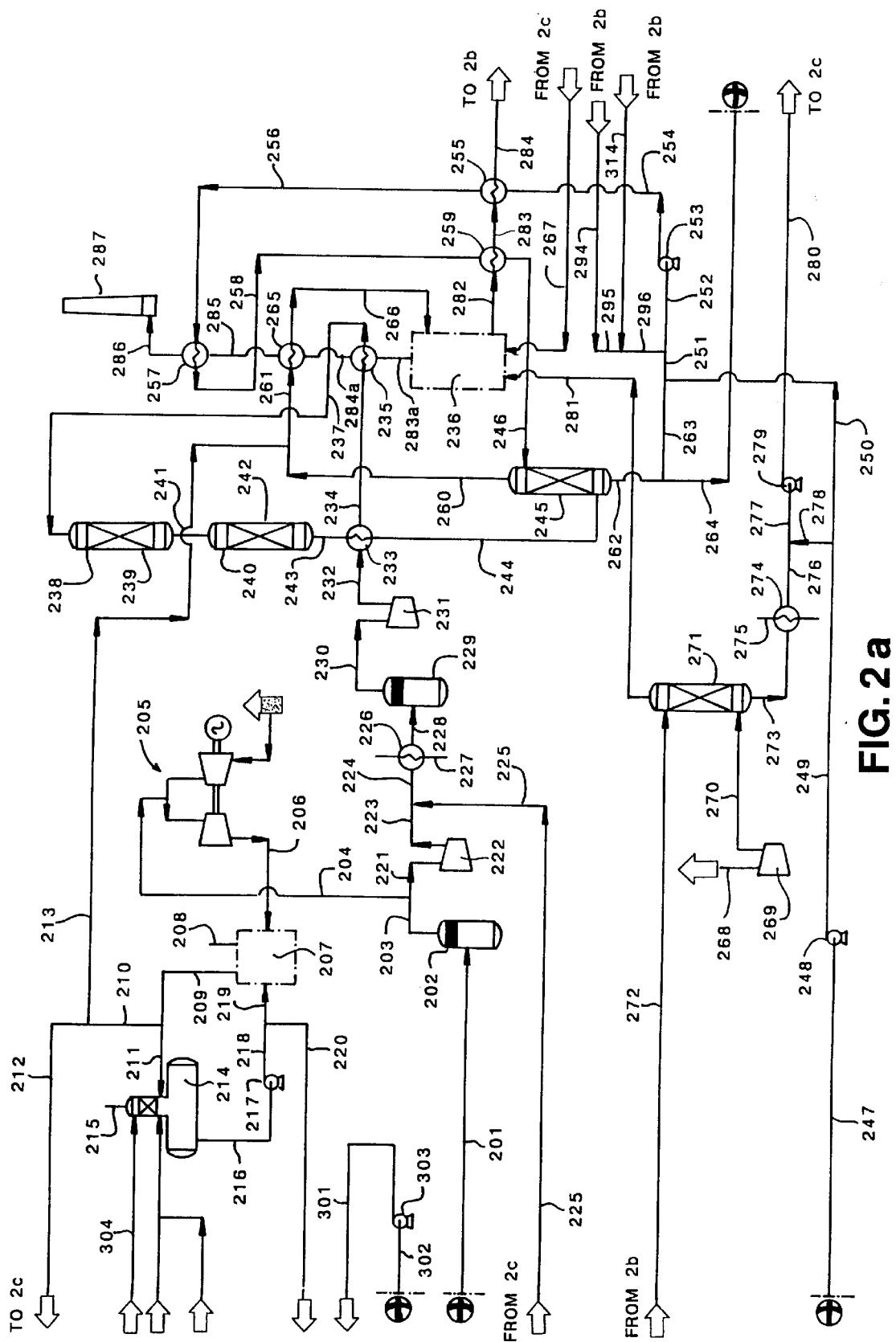
FIGS. 2a, 2b and 2c combine to show a more detailed flow diagram of a second methanol synthesis plant according to the invention.

Referring now to FIG. 2a, natural gas from battery limits is supplied to the plant in line 201 and enters natural gas knockout drum 202 before passing on in line 203. A portion of the gas in line 203 is taken in line 204 to power gas turbine 205.

Hot gas from gas turbine 205 passes along line 206 into heat recovery duct 207. Flue gas is vented to the atmosphere in line 208. Steam is withdrawn in line 209 and separated into two streams in line 210 and line 211. Steam in line 210 is further separated into two streams in line 212 and line 213. Steam in line 213 is supplied to the steam reforming process, as will be described later. Steam in line 212 is supplied to a methanol refining process, as will be described later. Steam in line 211 passes into deaerator 214, which is vented in line 215. Deaerated water is withdrawn in line 216 and passed via boiler water pump 217 into line 218. Water in line 218 passes on in line 219 and is fed to heat recovery duct 207. A make-up water stream is taken in line 220 and fed to a converter steam drum (not shown).

The remaining gas in line 203 passes on in line 221 and is compressed to around 25 bar in natural gas compressor 222. Compressed gas passes on in line 223 and combines in line 224 with a recycle stream from line 225. The combined stream in line 224 is cooled through interchanger 226 which is supplied with cooling water in line 227. The cooled stream passes on in line 228 and into knock out pot 229, where any condensate from the cooled stream is removed. The mixed gas stream then passes on in line 230 and is compressed to around 38 bar in recycle compressor 231.

The compressed gas stream passes on in line 232, is heated through interchanger 233, passes on in line 234 and is further heated through interchanger 235 which is mounted in the flue gas stream from reformer 236. Hot gas, now at a temperature of about 380° C., passes on in line 237 and into desulphurisation vessel 238 which contains a charge 239 of a suitable sulphurisation catalyst, such as nickel molybdate or cobalt molybdate. In the plant of FIG. 2a, zinc oxide is used as catalyst.

Gas from desulphurisation vessel 238 flows on in line 241 to desulphurisation vessel 240, which contains a charge 242 of a zinc oxide desulphurisation catalyst. The desulphurised gas stream, now containing less than about 0.1 parts per million of sulphur, flows on in line 243 through interchanger 233, where it is cooled, and passes via line 244 into the bottom of feed saturator 245.

Feed saturator 245 is supplied with hot water in line 246. Fresh water is supplied to the plant in line 247 and is pumped by pump 248 into lines 249, 250, 251 and 252, through pump 253 and into line 254. Water in line 254 is heated through interchanger 255 and is supplied in line 256 to interchanger 257. The heated water or steam passes on in line 258 to a further interchanger 259 and then into line 246.

In feed saturator 245 the mixed gas stream flows upwards and the hot water stream flows downwards. The gas leaves saturator 245 in line 260 containing around 90% of the steam required for downstream reforming reactions. The remaining 10% of steam is supplied in line 213 so that a gas stream containing 100% of the steam required for steam reforming passes on in line 261.

Water from the bottom of saturator 245 is recycled through lines 262 and 263 to combine in line 215 with Fresh water from line 250. A small blowdown taken from stream 262 passes on in line 264 for disposal. A warm water stream proceeds in lines 251 and 252 and is pumped by pump 253 into line 254, through interchanger 255, line 256, interchanger 257, line 258, interchanger 259 and into line 246 for supply to the top of saturator 245. The remainder of the blowdown stream from line 260 passes on in line 264 for disposal.

The gas stream in line 261 is heated in passage through interchanger 265 and passes on in line 266 to reformer 236. Interchangers 235, 265 and 257 are mounted in the flue gas duct of reformer 236. Interchangers 259 and 255 are mounted in the reformed gas duct of reformer 236. Reformer 236 comprises, in the plant shown in FIG. 2a, a number of compact reformer tubes arranged in parallel with each other. A reforming catalyst (not shown), such as a supported nickel catalyst, is provided within the reformer tubes. The feedstock and steam mixture from line 266, now at a temperature of about 400° C., passes into reformer 236 and flows therethrough from top to bottom.

The heat to drive the endothermic reforming reactions is supplied by burning a hydrogen-rich fuel inside reformer 236. Hydrogen fuel is supplied to reformer 236 in line 267. The fuel is recycled from a downstream separation process, as will be described later.

Combustion air for compact reformer 236 is supplied to the plant in line 268 and passes by means of air compressor 269 into line 270 and then into an air saturator column 271. The purpose of saturating the combustion air is to control the heat recovery inside compact reformer 236, to allow greater recovery of energy within the plant. Hot water is supplied to air saturator column 271 in line 272 after being recycled from a downstream refining step, as will be explained later. Water from the bottom of air saturator column 271 in line 273 is cooled in passage through heat exchanger 274 supplied with cooling water in line 275. The cooled water stream passes on in line 276 and is combined in line 277 with fresh water from line 278 before being pumped by pump 279 into line 280 for ultimate use in a downstream methanol recovery process, as will be described later. A saturated combustion air stream emerging from the top of air saturator column 271 is supplied to reformer 236 in line 281.

Figure 2B:
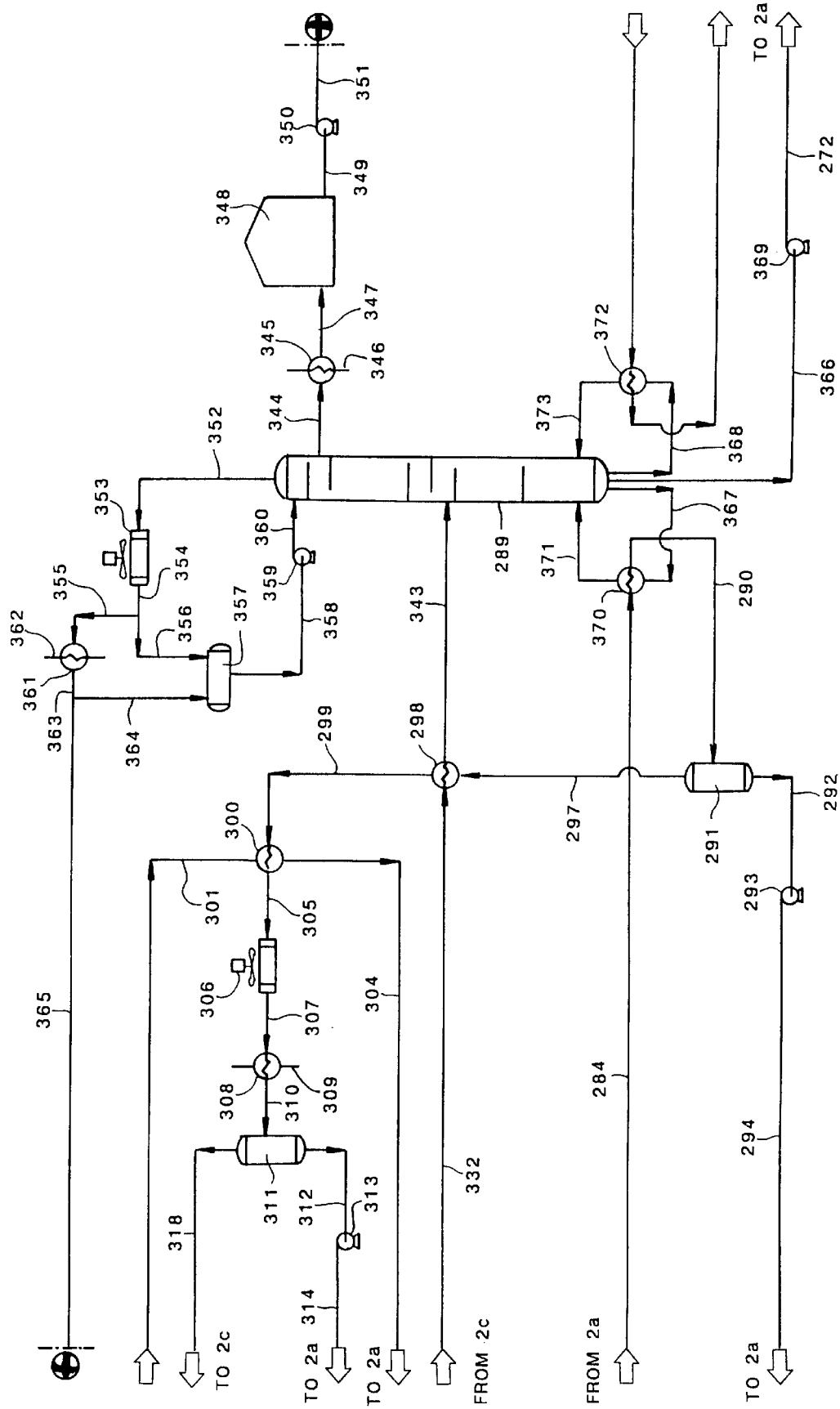
Figure 2C:
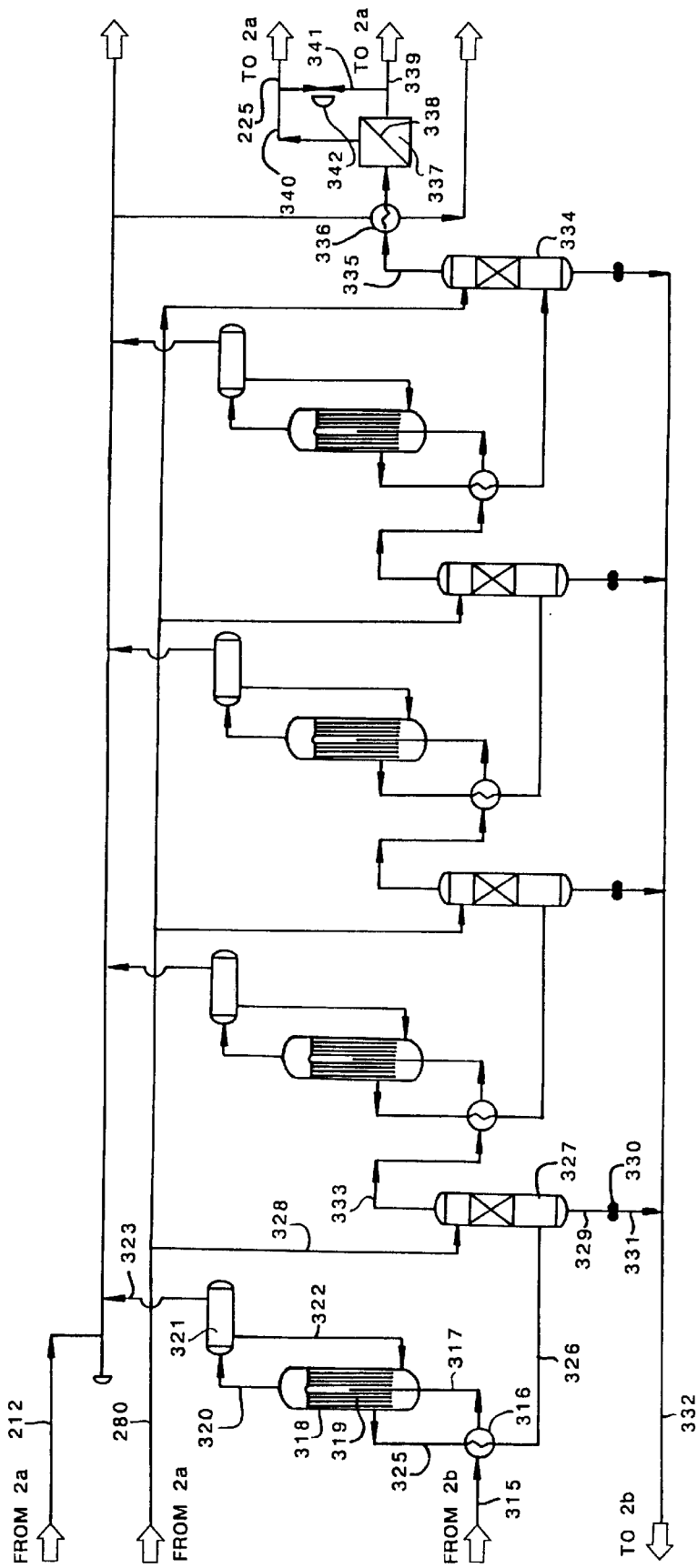

Although not shown in the plant of FIG. 2a, 2b and 2c, it is also possible to saturate the reformer fuel in line 267. It may be especially preferred to saturate the reformer fuel when the plant of the invention uses a compact reformer, of the type hereinbefore described.

The use of compact reformer 236 means that much of the heat generated within the reformer is recovered internally to reduce the overall fuel requirements of the plant. Also, reformed gas and flue gas from reformer 236 is used (in interchangers 255, 257 and 259) to heat the circulation water for the feed saturator 245. The water is heated first by reformed gas in saturator water heater 255, then by flue gas in saturator water heater 257 and finally by hot reformed gas in saturator water heater 259. The arrangement of heat exchangers can be modified to suit alternate reformer designs. The arrangement depicted in FIG. 2 takes advantage of the compact reformer to provide a heat recovery system with no "heat recycle" from the synthesis section to the reforming section. This makes plant start-up both easier and quicker than in conventional methanol plants.

A synthesis gas mixture, comprising carbon oxides, hydrogen and methane, is recovered from reformer 236 in line 282 and is cooled through interchanger 259, line 283 and interchanger 255 before passing on in line 284. The reformed gas stream exiting saturator water heater 255 is used to provide from about 35% to about 40% of the reboil heat for a downstream distillation column, as will be described later.

A flue gas stream exits reformer 236 in line 283a and exchanges heat with various streams in passage through interchanger 235, line 284a, interchanger 265, line 285 and interchanger 257 before passing into line 286. The flue gas stream leaves the plant via stack 287.

Referring now to FIG. 2b, synthesis gas in line 284 is further cooled in interchanger 370, by means of which reboil heat is supplied to distillation column 289. Cooled synthesis gas is passed by line 290 to knock out pot 291. Condensate from knock out pot 291 is supplied via line 292, pump 293 and line 294 to, and referring back now to FIG. 2a, line 295, line 296 and is then combined in line 252 with water from line 251. The combined stream in line 252 is eventually supplied to feed saturator column 245, as hereinbefore described.

Referring back to FIG. 2b, a synthesis gas mixture is recovered from the top of knock out pot 291 in line 297 and passes through interchanger 298 where it is cooled, supplying heat to a crude methanol stream supplied to distillation column 289, as will be described later. The cooled synthesis gas stream from interchanger 298 passes on in line 299. The stream in line 299 passes through interchanger 300, where it is used to pre-heat demineralised water for supply to the process as steam, as will be now be described.

Interchanger 300 is supplied in line 301 with demineralised water supplied to the plant via, and referring briefly back to FIG. 2a, line 302 and pump 303. Referring back to FIG. 2b, heated demineralised water passes on in line 304 and into, referring briefly back to FIG. 2a, deaerator 214.

Referring back to FIG. 2b, further cooled synthesis gas from interchanger 300 passes on in line 305 to gas cooler 306, line 307, interchanger 308 supplied with cooling water in line 309, into line 310 and is supplied to a second knockout pot 311. Condensate from knock out pot 311 is recovered in line 312 and is supplied, via pump 313 and line 314, to, and referring back to FIG. 2a, line 296 and is combined in line 252 with make-up water from line 250 and 251.

Referring back to FIG. 2b, synthesis gas emerging from the top of knock out pot 311 is supplied in line 315 to, and referring now to FIG. 2c, interchanger 316., through which it is pre-heated to a methanol synthesis temperature of about 210° C. before passing on in line 317 to methanol synthesis reactor 318 containing a charge 319 of a methanol synthesis catalyst, such as a copper/zinc catalyst, e.g. the catalyst sold under the designation Haldor Toopsoe MK-101. In the illustrated methanol converter 318, the exothermic heat of reaction is removed by raising steam in tubes mounted in the hot catalyst bed.

A circulation loop around methanol converter 318 is formed by line 320, converter steam drum 321 and line 322. Make-up water to the converter steam drum 321 is supplied from line 220 (FIG. 2a) via a connecting line (not shown). Product steam from converter steam drum 321 in line 323 is supplied to line 324, where it combines with steam from line 212, and is ultimately supplied as a reboiler heat to distillation column 289, as will be explained later.

A product gas mixture comprising methanol, carbon oxides, methane and hydrogen is recovered from methanol converter 318 in line 325. The stream in line 325 is cooled through interchanger 316 and passes on in line 326 to methanol wash column 327 which is supplied with wash water in line 328. If desired, an additional cooler (not shown) can be incorporated in line 326. Referring briefly to FIG. 2a, line 328 is supplied with wash water from line 280.

Crude methanol product is recovered from methanol wash column 327 in line 329 and is passed through a filter 330 into line 331 and on into line 332 for ultimate supply to a downstream refining step, as will be described later.

Synthesis gas mixture emerging from the top of methanol wash column 327 is passed in line 333 to a second methanol synthesis loop identical to the loop just described. A third and a fourth loop are also provided.

On exiting the fourth methanol wash column 334, unreacted synthesis gas mixture is supplied in line 335 to interchanger 336 and on into membrane separator 337. Hydrogen passes through membrane 338 and exits separator 337 in line 339, from where it passes on in line 267 to, and referring briefly to FIG. 2a, reformer 236. Carbon oxides and unreacted feedstock do not pass through membrane 338 and exit separator 337 in line 340.

A purge stream may be taken from line 340 in line 341 to control any build up of inert materials in the recycle stream. Purge line 341 is controlled by valve 342.

After the purge, if any, the recycle stream in line 340 passes on in line 225 and, referring back to FIG. 2a, is combined in line 224 with make-up natural gas from line 223.

Referring back to FIG. 2c, crude methanol product in line 332 is supplied, and referring now to FIG. 2b, via interchanger 298 to line 343. Crude methanol product in line 343 is supplied to the middle of a methanol refining column 289.

Refined methanol product is recovered from near the top of column 289 in line 344. The refined stream in line 344 is cooled through interchanger 345, supplied in line 346 by cooling water, and passes into line 347 and into methanol shift tank 348. Product methanol is recovered from shift tank 348 via line 349, pump 350 and line 351.

Vaporous material exits the top of column 289 in line 352 and is passed through condenser 353. Product from condenser 353 is recovered in line 354, which is vented in line 355. Unvented material flows on in line 35G to column reflux drum 357, before being recycled in line 358, via pump 359 and line 360, to the top of column 289. The vented stream in line 355 is cooled through heat exchanger 361, cooled by cooling water in line 362, and passes on in line 363 and line 354 to column reflux drum 357. Gas in line 363 could be recovered by suitable compression but here is vented in line 365 to the atmosphere.

A bottoms product is recovered from column 289 in lines 366, 367 and 368. The stream in line 366 is supplied via pump 369 to line 272 and, referring briefly back to FIG. 2a, to combustion air saturation column 271.

Referring back to FIG. 2b, bottoms product in line 367 is recycled to the bottom of column 289 via interchanger 370 and line 371. Bottoms product in line 368 is recycled to the bottom of column 289 via interchanger 372 and line 373.

What is claimed is:

1. A process for the production of methanol from a hydrocarbon feedstock comprising:
  a) contacting a vaporous mixture comprising the hydrocarbon feedstock and steam in a steam reforming zone with a catalyst effective for catalysis of at least one reforming reaction;
  b) recovering from the reforming zone a synthesis gas mixture comprising carbon oxides, hydrogen and methane;
  c) supplying material of the synthesis gas mixture to a methanol synthesis zone charged with a methanol synthesis catalyst and maintained under methanol synthesis conditions;
  d) recovering from the methanol synthesis zone a product gas mixture comprising methanol and unreacted material of the synthesis gas mixture;
  e) supplying material of the product gas mixture to a methanol recovery zone maintained under methanol recovery conditions;
  f) recovering from the methanol recovery zone a crude methanol product stream and a vaporous stream comprising unreacted material of the synthesis gas mixture;

g) separating material of the synthesis gas mixture into a first hydrogen-rich stream and a second hydrogen-depleted stream comprising carbon oxides and methane;

h) supplying at least part of the first hydrogen-rich stream to the steam reforming zone as fuel; and i) recycling at least part of the second hydrogen-depleted stream comprising carbon oxides and methane to the steam reforming zone to form part of the vaporous mixture of step a).

2. A process according to claim 1, wherein the separation step g) takes place downstream of the methanol synthesis zone, the at least part of the second hydrogen-depleted stream being supplied from the separation step g) to the reforming zone without passing through the methanol synthesis zone.

3. A process according to claim 1, wherein the separation step g) takes place upstream of the methanol synthesis zone, the at least part of the second hydrogen-depleted stream being supplied to the methanol synthesis zone, an unreacted part of the second hydrogen-depleted stream being recovered thereafter and supplied to the reforming zone.

4. A process according to any one of claim 1, wherein the methanol synthesis zone is maintained under a pressure of from about 20 bar to about 50 bar.

5. A process according to claim 4, wherein the methanol synthesis zone is maintained under a pressure of from about 25 bar to about 40 bar.

6. A process according to claim 5, wherein the methanol synthesis zone is maintained under a pressure of about 30 bar.

7. A process according to claim 1, wherein the separation of the first hydrogen-rich stream from the second hydrogen-depleted stream is achieved by means of a membrane separator.

8. A process according to claim 1, wherein the methanol synthesis zone comprises a plurality of methanol synthesis reactors connected in series, each successive pair of methanol synthesis reactors being separated by a methanol recovery zone, wherein the product gas mixture from each methanol synthesis reactor in the series is supplied to a corresponding methanol recovery zone and unreacted material of the synthesis gas mixture recovered from the methanol recovery zone is supplied to the next successive methanol synthesis reactor in the series.

9. A process according to claim 1, wherein the crude methanol product stream is supplied to a refining zone for recovery of a refined methanol product stream.

10. A process according to claims 1, wherein a single gas compressor is provided to drive the feedstock, synthesis gas and recycle streams.

11. A process according to claims 1, wherein the methanol synthesis zone is maintained at a temperature of from about 200° C. to about 300° C.

12. A process according to claims 1, wherein the feedstock comprises natural gas.

13. A plant for the production of methanol from a hydrocarbon feedstock material comprising:

a) a steam reforming zone, adapted to be maintained under steam reforming conditions and charged with a catalyst effective for catalysis of at least one steam reforming reaction, for steam reforming of a vaporous mixture of the hydrocarbon feedstock and steam to form a synthesis gas mixture comprising carbon oxides, hydrogen and methane;

b) a methanol synthesis zone, adapted to be maintained under methanol synthesis conditions and charged with a methanol synthesis catalyst, for conversion of material of the synthesis gas mixture to a product gas mixture comprising product methanol and unreacted material of the synthesis gas mixture;

c) a methanol recovery zone, adapted to be maintained under methanol recovery conditions, for recovery of a crude methanol product stream from the product gas mixture, and for recovery of a vaporous stream comprising unreacted material of the synthesis gas mixture;

d) a separation zone for separation of material of the synthesis gas mixture into a first hydrogen-rich stream and a second hydrogen-depleted stream comprising carbon oxides and methane;

e) means for supplying at least part of the first hydrogen-rich stream to the steam reforming zone as fuel; and f) means for recycling at least part of the second hydrogen-depleted stream comprising carbon oxides and methane to the steam reforming zone for admixture with the vaporous mixture of hydrocarbon feedstock and steam.

14. A plant according to claim 13, wherein the separation zone is located downstream of the methanol synthesis zone, means being provided for supplying the at least part of the second hydrogen-depleted stream from the separation zone to the reforming zone without passing through the methanol synthesis zone.

15. A plant according to claim 13, wherein the separation zone is located upstream of the methanol synthesis zone, means being provided for supplying the at least part of the second hydrogen-depleted stream to the methanol synthesis zone and thereafter recovering an unreacted part of the second hydrogen-depleted stream and supplying the unreacted part to the reforming zone.

16. A plant according to claim 13, wherein the separation zone comprises a membrane separator.

17. A plant according to claim 13, wherein a plurality of methanol synthesis zones are provided in series with a plurality of methanol recovery zones, the recycle stream from each methanol recovery zone, other than the last in the series, being supplied to a next successive methanol synthesis zone in the series.

18. A plant according to claim 13, wherein there is further provided a refining zone, maintained under refining conditions, having an inlet for supply of the crude methanol product stream and an outlet for recovery of a refined methanol product stream.

19. A plant according to claim 13, wherein a single gas compressor is provided to drive the feedstock, synthesis gas and recycle streams.

* * * * *